(12) United States Patent
Chen et al.

(10) Patent No.: US 9,030,159 B2
(45) Date of Patent: May 12, 2015

(54) INDUCTIVE CHARGER WITH MAGNETIC SHIELDING

(75) Inventors: Joey Chen, Valencia, CA (US); Robert Ozawa, Woodland Hills, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 868 days.

(21) Appl. No.: 13/040,945

(22) Filed: Mar. 4, 2011

(65) Prior Publication Data

US 2011/0234155 A1    Sep. 29, 2011

Related U.S. Application Data

(60) Provisional application No. 61/318,143, filed on Mar. 26, 2010.

(51) Int. Cl.
| | | |
|---|---|---|
| *H02J 7/00* | (2006.01) | |
| *A61N 1/378* | (2006.01) | |
| *H01F 27/36* | (2006.01) | |
| *H01F 38/14* | (2006.01) | |
| *H02J 7/02* | (2006.01) | |

(52) U.S. Cl.
CPC .............. *A61N 1/3787* (2013.01); *H01F 27/365* (2013.01); *H01F 38/14* (2013.01); *H02J 7/025* (2013.01)

(58) Field of Classification Search
USPC .......................................................... 320/108
See application file for complete search history.

(56) References Cited

U.S. PATENT DOCUMENTS

| | | | |
|---|---|---|---|
| 4,071,032 A * | 1/1978 | Schulman | ........................ 607/36 |
| 6,324,430 B1 | 11/2001 | Zarinetchi et al. | |
| 6,324,431 B1 | 11/2001 | Zarinetchi et al. | |
| 6,389,318 B1 | 5/2002 | Zarinetchi et al. | |

(Continued)

FOREIGN PATENT DOCUMENTS

| | | |
|---|---|---|
| JP | 2-79583 | 6/1990 |
| JP | 05-317433 | 3/1993 |

(Continued)

OTHER PUBLICATIONS

International Search Report and Written Opinion regarding corresponding application No. PCT/US2011/028071, dated May 24, 2011.

(Continued)

*Primary Examiner* — Drew A Dunn
*Assistant Examiner* — Steve T Chung
(74) *Attorney, Agent, or Firm* — Lewis & Reese, PLLC (57) ABSTRACT

To recharge an implanted medical device, an external device, typically in the form of an inductive charger, is placed over the implant to provide for transcutaneous energy transfer. The external charging device can be powered by a rechargeable battery. Since the battery is in close proximity to the charge coil, the large magnetic field produced by the charge coil induces eddy currents that flow on the battery's metallic case, often resulting in undesirable heating of the battery and reduced efficiency of the charger. This disclosure provides a means of shielding the battery from the magnetic field to reduce eddy current heating, thereby increasing efficiency. In one embodiment, the magnetic shield consists of one or more thin ferrite plates. The use of a ferrite shield allows the battery to be placed directly over the charge coil as opposed to outside the extent of the charge coil.

23 Claims, 8 Drawing Sheets

(56) References Cited

U.S. PATENT DOCUMENTS

| | | | |
|---|---|---|---|
| 6,496,733 B2 | 12/2002 | Zarinetchi et al. | |
| 6,553,263 B1 * | 4/2003 | Meadows et al. | 607/61 |
| 6,850,803 B1 * | 2/2005 | Jimenez et al. | 607/61 |
| 7,225,032 B2 * | 5/2007 | Schmeling et al. | 607/61 |
| 7,286,880 B2 * | 10/2007 | Olson et al. | 607/61 |
| 7,286,881 B2 * | 10/2007 | Schommer et al. | 607/61 |
| 7,505,816 B2 | 3/2009 | Schmeling et al. | |
| 8,005,547 B2 * | 8/2011 | Forsberg et al. | 607/33 |
| 2002/0043957 A1 | 4/2002 | Krainer | |
| 2005/0075696 A1 | 4/2005 | Forsberg et al. | |
| 2005/0113889 A1 | 5/2005 | Jimenez et al. | |
| 2007/0038250 A1 | 2/2007 | He et al. | |
| 2008/0027500 A1 | 1/2008 | Chen | |
| 2009/0036944 A1 * | 2/2009 | Fonte | 607/36 |
| 2009/0118796 A1 | 5/2009 | Chen et al. | |
| 2010/0036458 A1 | 2/2010 | Duftner et al. | |
| 2010/0204756 A1 | 8/2010 | Aghassian | |
| 2011/0004278 A1 | 1/2011 | Aghassian et al. | |

FOREIGN PATENT DOCUMENTS

| | | | |
|---|---|---|---|
| JP | 08016745 A * | 1/1996 | G06K 19/07 |
| JP | 2000-183583 | 6/2000 | |
| WO | 2010133995 | 11/2010 | |

OTHER PUBLICATIONS

U.S. Appl. No. 12/562,694, filed Sep. 18, 2009, Aghassian.
Examination Report regarding corresponding Australian application No. 2011229869, dated Feb. 12, 2013.

* cited by examiner

INDUCTIVE CHARGER WITH MAGNETIC SHIELDING

CROSS REFERENCE TO RELATED APPLICATIONS

The present application claims the benefit of U.S. Provisional Patent Application Ser. No. 61/318,143, filed Mar. 26, 2010, which is incorporated herein by reference in its entirety.

FIELD OF THE INVENTION

The present invention relates to an improved wireless external charger for more efficiently charging an implantable medical device, wherein the external charger comprises a magnetic shield. The invention also provides an integrated and compact, low-profile charger design that contains a battery, coil, and magnetic shield, all co-axially aligned in a single, self-contained housing.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Patent Publication 2007/0038250.

Figure 1:
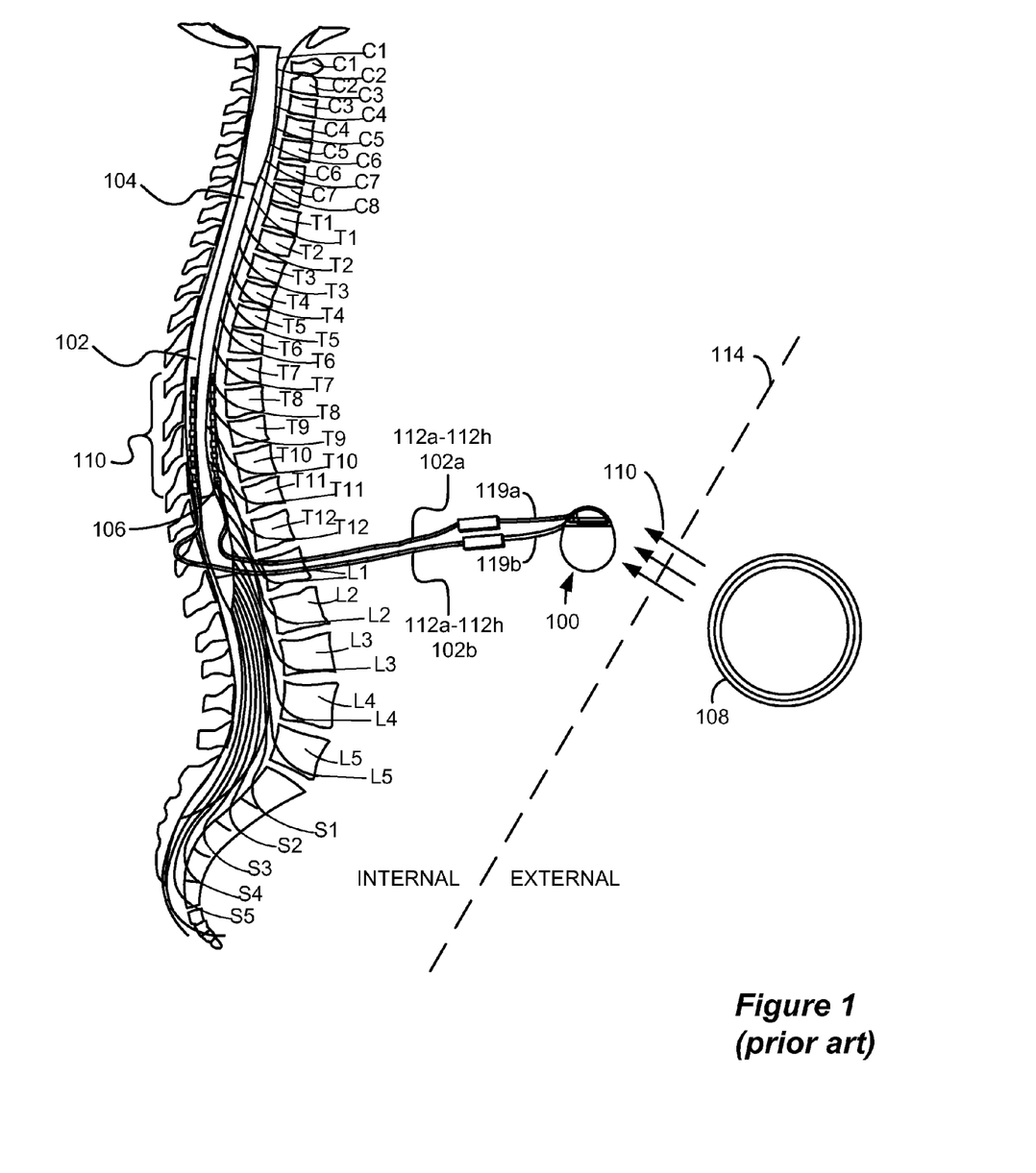
FIG. 1 shows an implantable pulse generator (IPG), an external charging coil, and the manner in which an electrode array is coupled to the IPG, in accordance with the prior art.

Spinal cord stimulation is a well-accepted clinical method for reducing pain in certain populations of patients. An SCS system typically includes an Implantable Pulse Generator (IPG), electrodes, at least one electrode lead, and, optionally, at least one electrode lead extension. As shown in FIG. 1, the electrodes 106, which reside on a distal end of the electrode lead 102, are typically implanted along the dura 102 of the spinal cord 104, and the IPG 100 generates electrical pulses that are delivered through the electrodes 106 to the nerve fibers within the spinal column 104. Electrodes 106 are arranged in a desired pattern and spacing to create an electrode array 110. Individual wires 112 within one or more electrode leads 102 connect with each electrode 106 in the array 110. The electrode lead(s) 102 exit the spinal column 104 and may attach to one or more electrode lead extensions 119a and 119b. The electrode lead extensions 119a and 119b, in turn, are typically tunneled around the torso of the patient to a subcutaneous pocket where the IPG 100 is implanted. Alternatively, the electrode lead 102 may directly connect with the IPG 100.

As should be obvious, an IPG needs electrical power to function. Such power can be provided in several different ways, such as through the use of a rechargeable or non-rechargeable battery or through electromagnetic (EM) induction provided from an external charger, or from combinations of these and other approaches, which are discussed in further detail in U.S. Pat. No. 6,553,263. Perhaps the favorite of these approaches is to use a rechargeable battery in the IPG, such as a Lithium-ion battery or a Lithium-ion polymer battery. Such a rechargeable battery can generally supply sufficient power to run an IPG for a sufficient period (e.g., a day or more) between recharging. Recharging can occur through the use of EM induction, in which EM fields are sent by an external charger to the IPG. Thus, when the battery in the IPG needs recharging, the patient in which the IPG is implanted can activate the external charger to transcutaneously (i.e., through the patient's flesh 114) charge the battery (e.g., at night when the patient is sleeping or during other convenient periods). In FIG. 1A, the external charger is represented generically by coil 108, which coil can be used to produce an EM field 110 capable of transcutaneous transmission through the patient's flesh 114.

Figure 2:
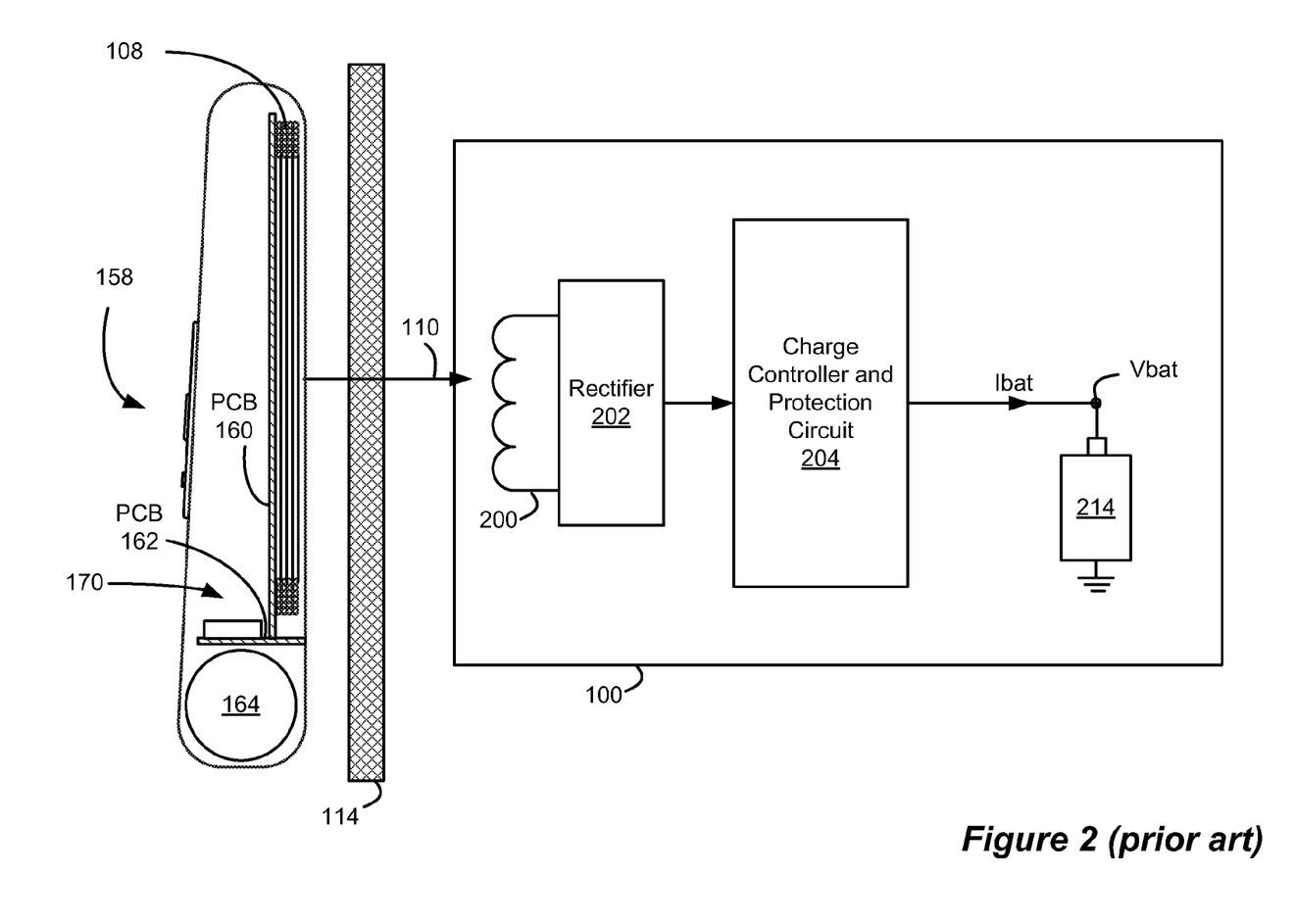
FIG. 2 illustrates a prior art system comprising an external charger for charging an implantable pulse generator, including the charge controller and battery protection aspects of the IPG.

Several basic varieties of external charger designs possessing a charging coil (such as coil 108) have been disclosed in the prior art. See, e.g., U.S. Patent Publication 2009/0118796; U.S. Patent Publication 2010/0204756; and U.S. Patent Publication 2008/027500. The operation of these prior art external chargers function essentially as shown in FIG. 2. As shown, the system comprises, in relevant part, the external charger 158 and IPG 100. A primary coil 108 in the charger 158 produces an EM field 110 capable of transcutaneous transmission through a patient's flesh 114. The EM field 110 is met at the IPG 100 by another coil 200, and accordingly, an AC voltage is induced in that secondary coil 200. This AC voltage in turn is rectified to a DC voltage at a rectifier 202, which may comprise a standard bridge circuit. (There may additionally be data telemetry associated with the EM field 110, but this detail is ignored as impertinent to the present disclosure). The rectified DC voltage is, in turn, sent to a charge controller and protection circuit 204, which operates generally to regulate the DC voltage and to produce either a constant voltage or constant current, Ibat, output as necessary for recharging the IPG 100's internal rechargeable battery 206. Further details concerning external chargers can be found in the '955 application.

Figure 3:
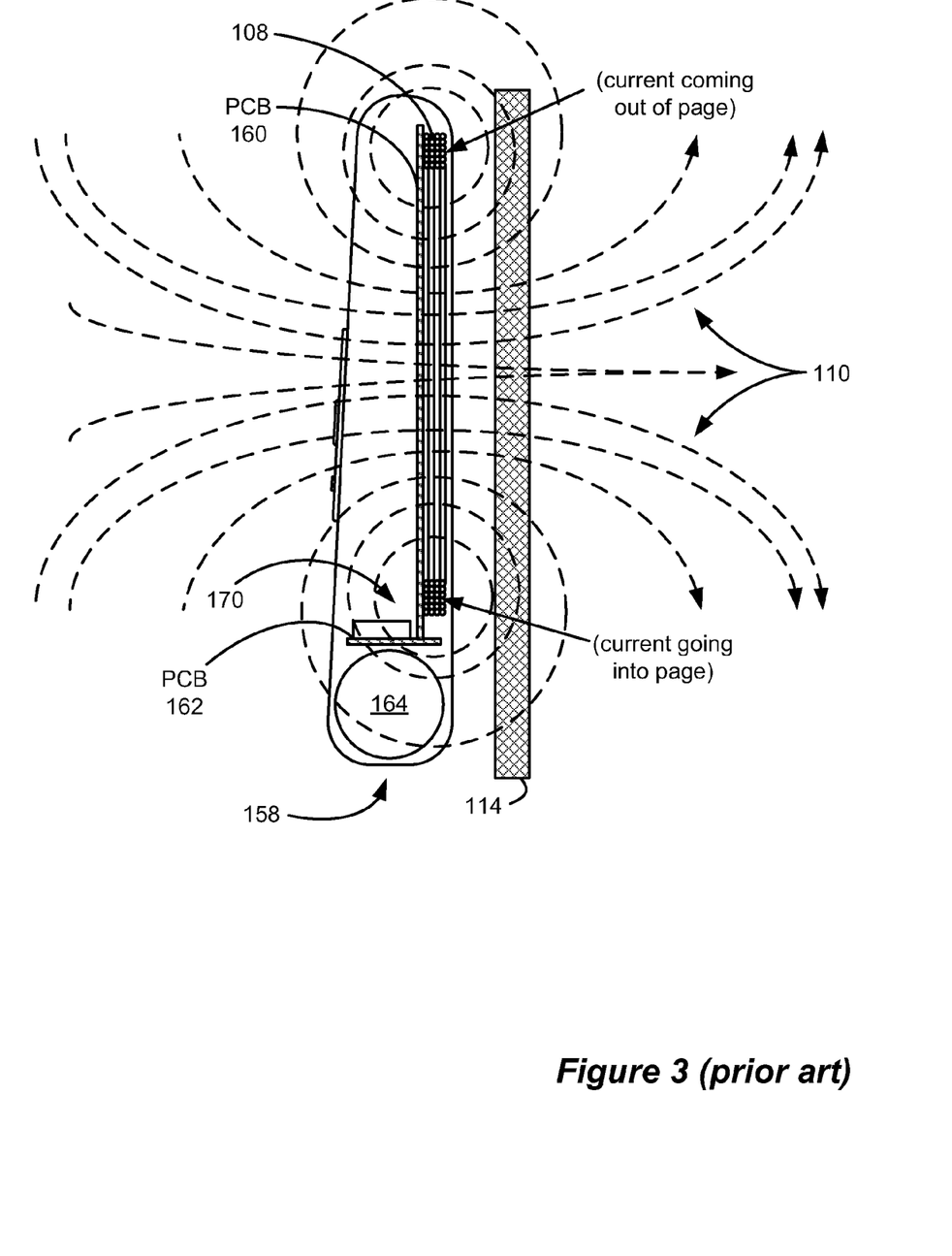
FIG. 3 shows a side view of representative magnetic field lines generated by a prior art external charger for an implantable medical device.

As shown in FIG. 3, electrical current flowing into the page at the lower end of coil 108 and out of the page at the upper end of coil 108 induces a magnetic field 110 having a prominent portion in a direction perpendicular to the plane in which the primary coil 108 lies. Primary coil 108 is typically formed of many turns of copper Litz wire, of which only a handful of individual turns are shown in FIG. 3 for clarity. Thus, when a face of the case of the external charger 158 is oriented in close proximity to an implanted device, such that the primary coil 108 is parallel to a corresponding secondary coil 200 within the IPG 100, the magnetic field generated by the primary coil 108 induces an electrical current within corresponding coil 200 to charge the battery 214 within, or otherwise provide power, to the IPG 100.

As shown in FIG. 3, the magnetic field generated by an unshielded primary coil generates a magnetic field which is in part directed toward the secondary coil where it performs useful work, and which is in part directed away from the secondary coil where the magnetic field energy is substantially wasted. If a higher percentage of the magnetic field from the primary coil could be directed to the implanted secondary coil, the energy required to drive the external charger could be reduced, which could allow the external charger to be made smaller. One such method of directing a higher percentage of the magnetic field from the primary coil towards the body is to use a magnetic field shield behind the primary coil's windings, such as is illustrated in U.S. Pat. No. 6,389,318. Such a design can enhance the energy transferring efficiency of the external charger/implantable device system by reflecting magnetic field lines back inwards. The magnetic field shield can be constructed of any material with a high permeability, such as, but not limited to, ferrite powder or ferrite plates.

Heretofore, attempts at producing a wireless and integrated (i.e., containing a power source, charging coil, and associated charging and/or telemetry circuitry in a single, self-contained package), compact, and low-profile external charger were complicated by the generation of excessive heating and eddy currents in the casing of the external charger's power source, usually a rechargeable battery. In the state of the art charging device, the external charger's battery is placed near the charging coil inside the charging device. Due to this close proximity, the magnetic field produced by the charge coil induces eddy current heating in the battery case. This has the undesirable effect of both additional device heating as well as reduced charging efficiency. As much as 20% of the power transmitted by the charge coil is lost due to this coupling between the charge coil and the battery.

Given these shortcomings, the art of implantable devices would benefit from an improved wireless external charger design that is integrated, compact, and low-profile, that also comprises a magnetic shield. Such a charger would provide for: increased charging efficiency; faster charging rates; increased patient safety and comfort; lower power requirements; and a smaller form factor. This disclosure presents a solution to this problem, disclosing an external charger comprising: a housing; a coil within the housing; a rechargeable battery within the housing; and a magnetic shield within the housing comprising a plate or plates made of a high permeability material, wherein the magnetic shield is located between the battery and the coil, wherein the coil, battery, and magnetic shield are co-axially aligned, and wherein the coil is used to provide power to an implantable medical device.

DETAILED DESCRIPTION

The description that follows relates to use of the invention within a spinal cord stimulation (SCS) system. However, it is to be understood that the invention is not so limited. Rather, the invention may be used with any type of implantable medical device that could benefit from improved charging between an external charger and the implantable device. For example, the present invention may be used as part of a system employing an external charger configured to charge a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover, the technique can be used in non-medical and/or non-implantable devices or systems as well, i.e., in any device or system in which improved coupling between a primary and second device is necessary or desirable.

To recharge an implanted medical device, an external device, typically in the form of an inductive charger, is placed over the implant to provide for transcutaneous energy transfer. The external charging device can be powered by a rechargeable battery. Since the battery is in close proximity to the charge coil, the large magnetic field produced by the charge coil induces eddy currents that flow on the battery's metallic case, often resulting in undesirable heating of the battery and reduced efficiency of the charger. This disclosure provides a means of shielding the battery from the magnetic field to reduce eddy current heating, thereby increasing efficiency. In one embodiment, the magnetic shield consists of one or more thin ferrite plates. The use of a ferrite shield allows the battery to be placed directly over the charge coil as opposed to outside the charge coil. In another embodiment, the magnetic shield consists of a battery-enclosing box consisting of one or more thin ferrite plates. The use of a ferrite box allows the battery to be placed completely within the extent of the charge coil.

Figure 4:
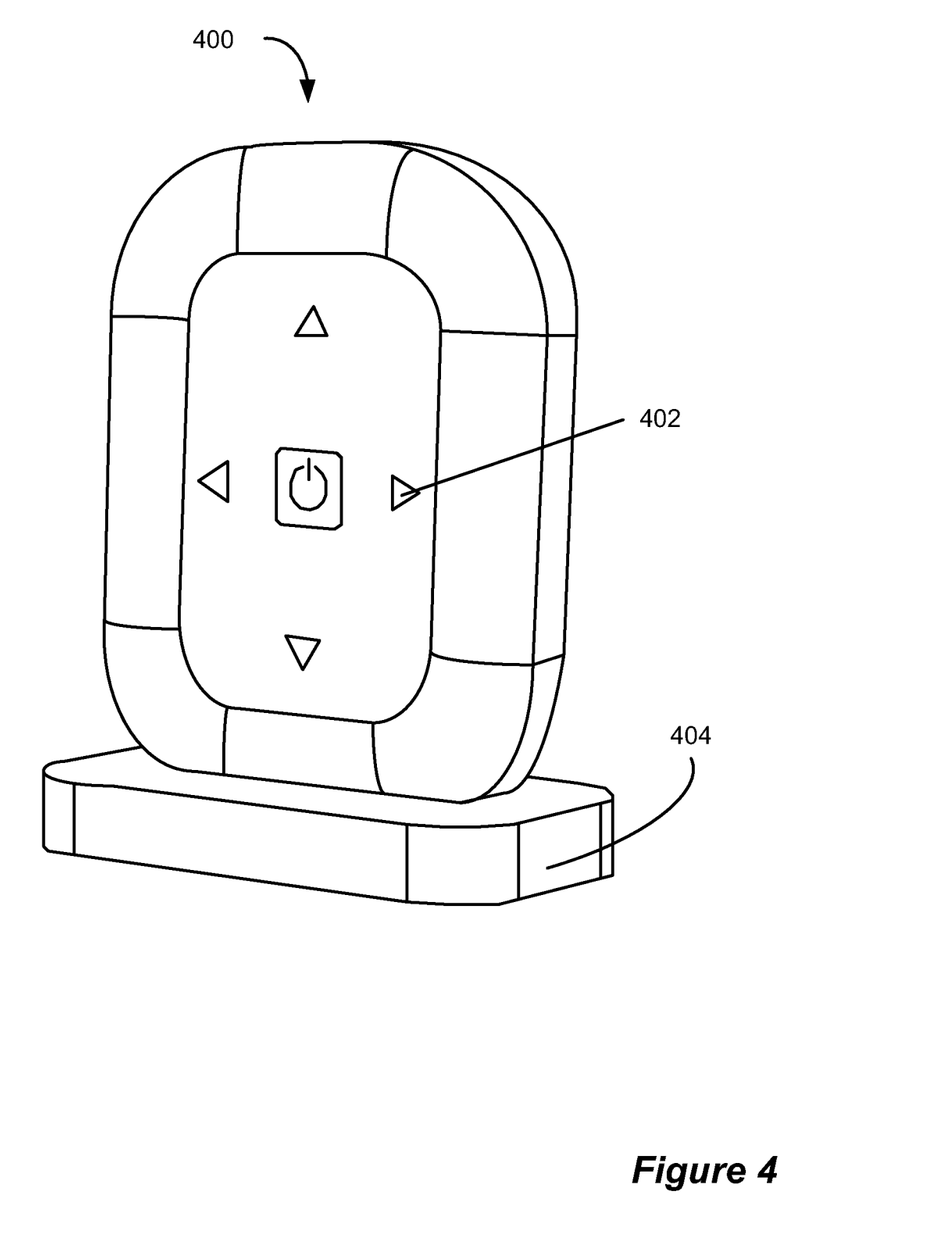
FIG. 4 shows one embodiment of an improved external charger for charging an implantable pulse generator

FIG. 4 shows one embodiment of an improved external charger 400 for charging an implantable device that is integrated, compact, low-profile, wireless, and contains a battery, coil, and magnetic shield, all co-axially aligned within the single, self-contained housing. The external charger 400 is shown sitting in a base unit 404 that may be used for charging the external charger 400. In this embodiment, four arrow-shaped LED lights 402 are arranged on the surface of the external charger 400, with one arrow-shaped LED light pointing towards each edge of external charger 400. The LED lights 402 can, in some implementations, be used to help the patient better align the external charger 400 with the implantable device 100, as is explained further in U.S. Patent Publication 2011/0004278.

Figure 5A:
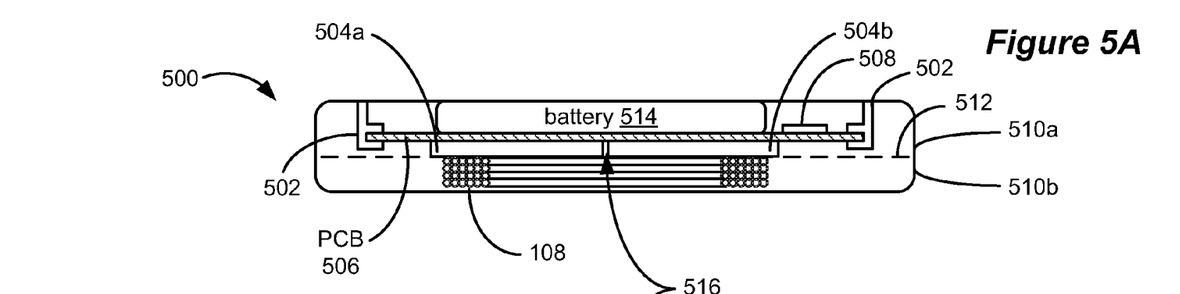
FIGS. 5A and 5B show side and bottom views of one possible embodiment of an improved external charger for an implantable medical device wherein the magnetic shield comprises one or more tiled ferrite plates.
Figure 5B:
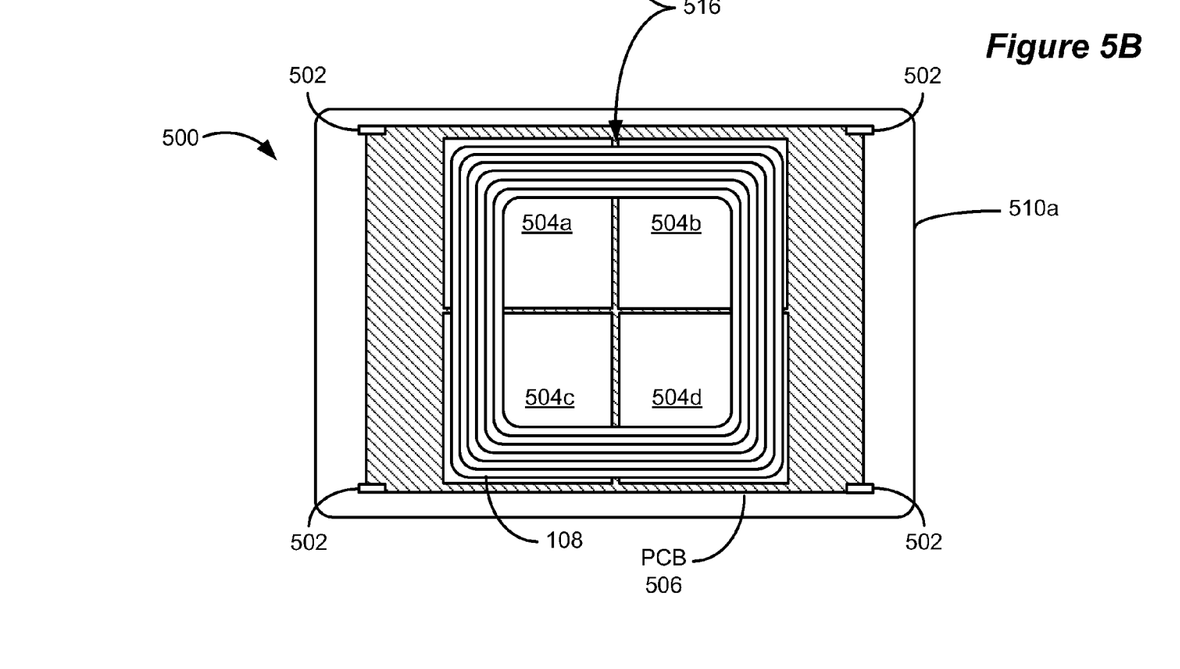

FIGS. 5A and 5B show side and bottom views, respectively, of the internal components of one possible embodiment of an improved external charger 500 for an implantable medical device that is similar in form factor to the external charger 400 shown in FIG. 4. Charger 500 is an integrated and compact, low-profile, wireless external charger design that contains a battery 514, a coil 108, and a magnetic shield 504, all co-axially aligned, in a single stack. Magnetic shield in this embodiment comprises one or more tiled ferrite plates 504. As shown in FIG. 5A, the external charger 500 also consists of a case or housing 510, typically formed of a hard plastic, which may be divided into top half 510a and bottom half 510b along a central axis 512. Clamps 502 may be utilized to hold a printed circuit board 506 in place mechanically. Clamps 502 are shown formed as a part of the top case half, although this is not strictly necessary, as other means can be used to stabilize the components within the case 510. Associated electronic circuitry 508 may be printed onto PCB 506 in any desired location, but preferably behind magnetic shield 504 so as to minimize the generation of any eddy currents in the associated electronic circuitry 508. Battery 514 can be placed on the opposite side of PCB 506 from the coil 108. A thin prismatic battery rather than a cylindrical battery can be used in the charger, allowing for a low-profile charger package. For example, Lithium-ion battery Model No. CGA633450B from PANASONIC® provides a 3.7V/1200 mAh power source that has dimensions of 34.0 mm wide, 50.0 mm long, and just 6.3 mm thick.

Since the battery 514 in the charger 500 depicted in FIGS. 5A-5B is in close proximity to the charge coil 108, the large magnetic field produced by the charge coil would, in the absence of a magnetic shield, tend to induce eddy currents to flow on the battery's 514 metallic case, which is typically constructed of aluminum or steel. These eddy currents act to oppose the magnetic field produced by coil 108 and create unnecessary heating of the battery 514 as well as reduced efficiency of the charger 500. Therefore, one embodiment of an improved external charger 500 design provides a means of shielding the battery from the magnetic field to reduce eddy current heating, thereby increasing efficiency of the charger 500. In the depicted embodiment, the magnetic shield comprises one or more ferrite plates 504, but preferably four to six plates. The ferrite plates can have any shape, although preferably are square or rectangular to allow for placement in a tiled pattern. As shown in FIG. 5B, the magnetic shield may consist of four square plates, 504a-504d. The ferrite plates 504 can be, for example, Model No. HP1040-100 from LAIRD TECHNOLOGIES®, which measure 26.42 mm to a side and are 1.27 mm thick. Each plate also has an adhesive backing that allows for easy and simple application to a surface, such as PCB 506, if so desired. The gaps 516 between the plates 504 are preferably relatively small, ideally less than 1 mm, so as to prevent significant flux leakage through the gaps. The primary advantage of having several small plates rather than one large plate is a smaller plate is structurally stronger than one large plate, as ferrite is somewhat brittle. Also, the cost to manufacture multiple small plates may be lower than the costs to manufacture a single, large plate, especially when the ferrite used is very thin. Alternatively, the ferrite plates 504 could comprise "78 Material," such as that produced by FAIR-RITE® Products Corp., which is a MnZn (Manganese-Zinc) ferrite specifically designed for power applications at frequencies up to 200 kHz. In the current application, charging of the implant is preferably done in a range between 80 kHz and 120 kHz, and, thus, 78 Material is an excellent choice due to its high permeability (approximately 2,000) in this frequency range.

The charge coil 108 can then be adhered to the ferrite plates 504, with the battery 514, as mentioned before, placed on the opposite side of the PCB 506. In other embodiments (not shown), the ferrite plates can be placed on the side of the PCB 506 where the battery is located, opposite the side of coil 108. The use of a ferrite shield 504 also allows the battery 514 to be placed directly over the charge coil 108 as opposed to outside the extent of the charge coil 108.

Without the magnetic shield comprising the tiled ferrite plates 504a-504d, the external charger 500 would experience significant decreases in charging efficiency. Because battery 514 has a metal casing, eddy currents would be generated in the battery casing by the induced magnetic field 110 of coil 108, and such eddy currents would create an opposing magnetic field. These eddy currents will result in energy being transferred to the metal battery case in the form of heating losses. Thus, the external charger would be losing efficiency because of the power being dissipated in the battery 514's case. This would cause the implanted medical device 100 to not charge as quickly, and/or cause the battery 514 in the external charger 500 to deplete faster While the magnetic field induced by the eddy currents may only be on the order of about 5% of magnetic field 110 induced by coil 108, these negative effects would still be significant. Additionally, the heat resulting from the eddy currents is unwanted.

Figure 6:
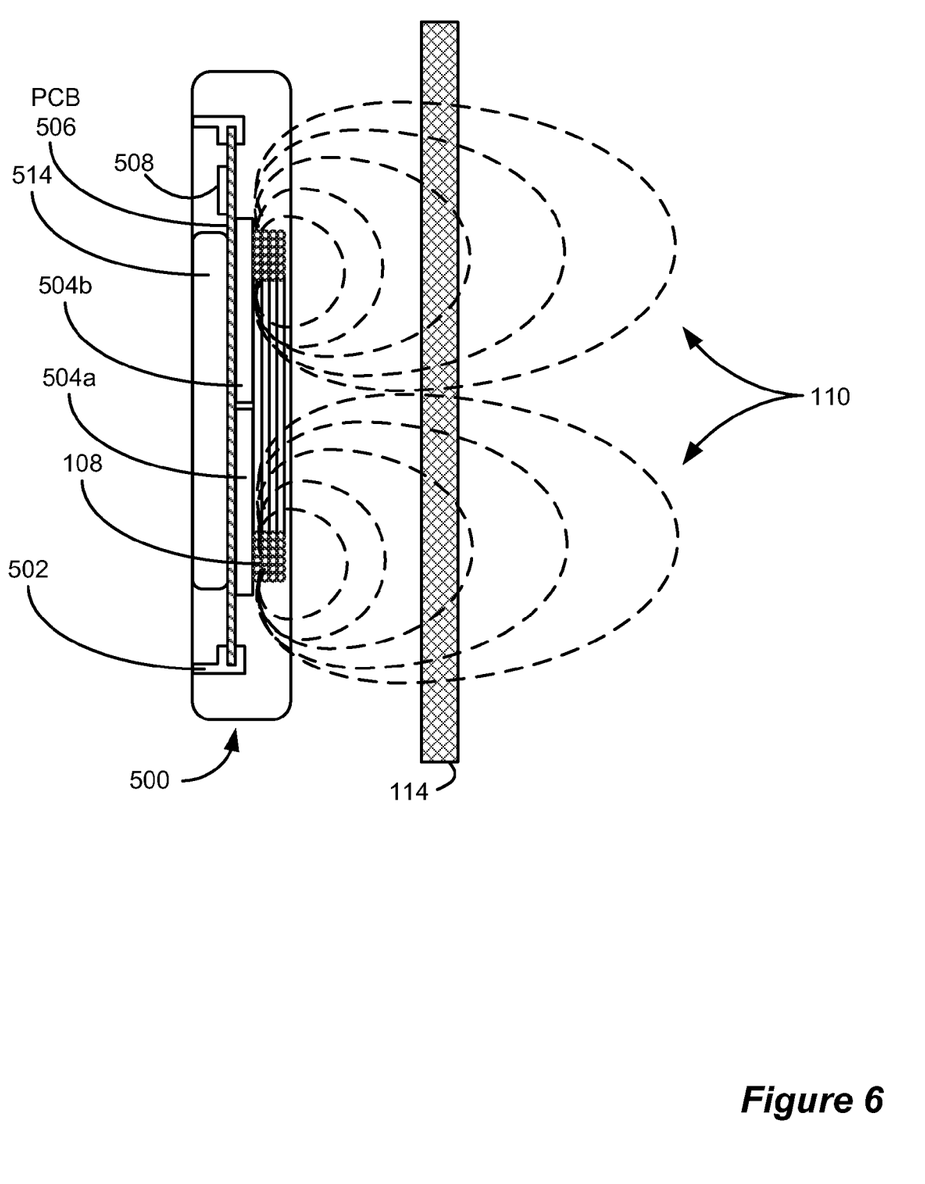
FIG. 6 shows a side view of representative magnetic field lines generated by the external charger of FIGS. 5A and 5B.

However, when the ferrite plates 504 are used, these negative effects are lessened. As shown in FIG. 6, the increased permeability of the ferrite plates 504 causes the magnetic field lines inside the ferrite to flow in a plane parallel with the coil 108 instead of perpendicular to the coil 108, thus diverting the magnetic field from reaching the battery 514. Additionally, the ferrite plates 504 increases the overall efficiency of the charging system due to fewer magnetic field lines being directed away from the patient's body, where the magnetic field energy is substantially wasted (compared FIG. 3). Due to the placement of magnetic shield 504, a higher percentage of the magnetic field 110 from the primary coil 108 is directed towards the implanted secondary coil (not shown) across skin boundary 114. The relative permeability of the ferrite shield, which is typically in the range of 500 to 5000, can increase the quality factor of the coil 108 by as much as 50% due at least in part to the "reflection" of magnetic flux back towards the patient's implanted device.

Figure 7A:
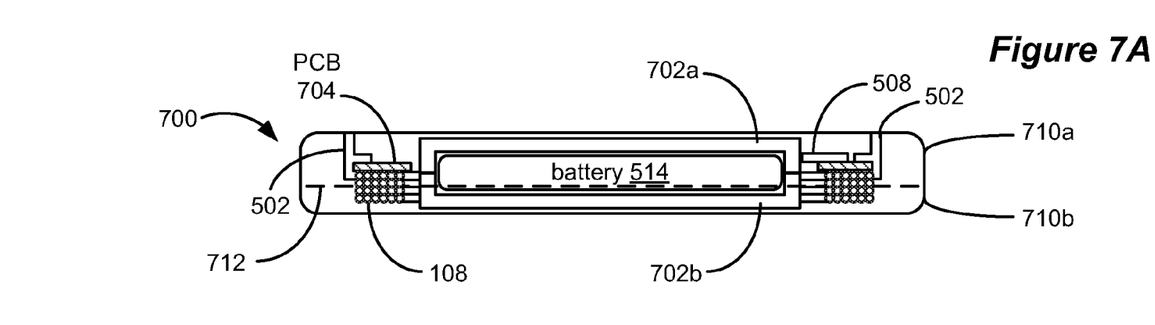
FIGS. 7A and 7B show side and bottom views of one possible embodiment of an improved external charger for an implantable medical device wherein the magnetic shield comprises a battery-enclosing box constructed of one or more ferrite plates.
Figure 7B:
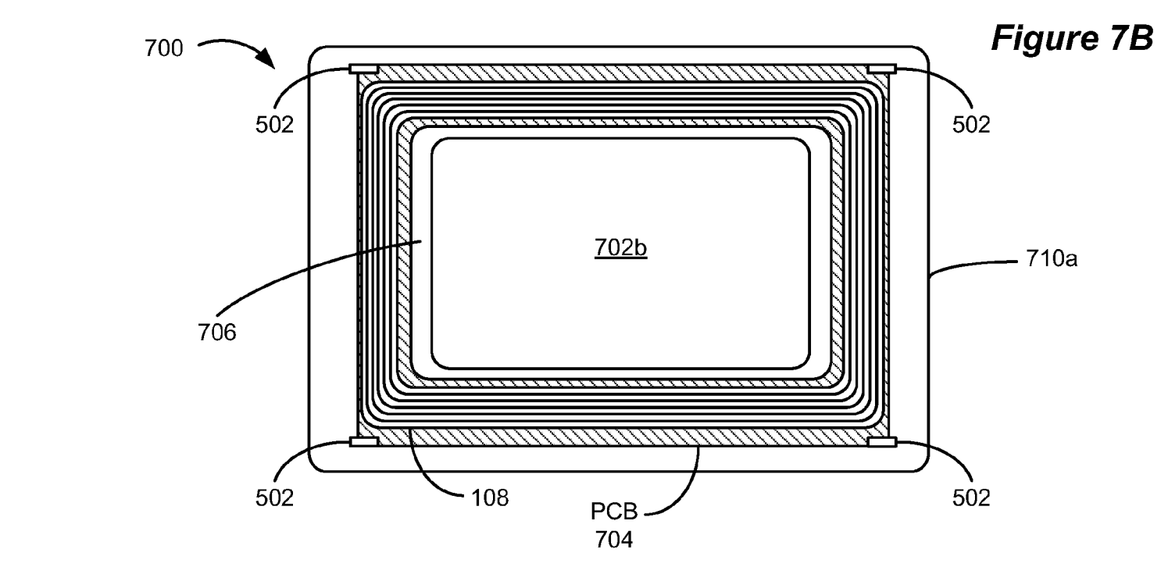

FIGS. 7A and 7B show side and bottom views of an alternative embodiment of an improved external charger 700 for an implantable medical device that is similar in form factor to the external charger 400 shown in FIG. 4. In this embodiment, the magnetic shield comprises a battery-enclosing ferrite box 702 constructed of a material with good magnetic shielding properties, i.e., a material with high permeability such as those discussed earlier. In this alternative embodiment, the ferrite box 702 covers the battery 514 from all sides. However, because the box may be made with plates as in the earlier embodiment, the ferrite box 702 may contain small gaps which would not significantly alter their functionality.

External charger 700 is similar in design to external charger 500 of FIGS. 5A-5B. However, in contrast to the design of external charger 500, and as just mentioned, the battery 514 of external charger 700 is placed inside the ferrite box 702. The ferrite box 702 can be composed of two clamshell plates that enclose the battery, e.g., 702a and 702b, or multiple plates arranged in a tiled pattern that enclose the battery on all sides. One advantage of this embodiment is that the housing 710 can be made thinner since the charge coil 108 does not lie on the ferrite box 702 (compare FIGS. 5A and 5B), but rather surrounds it. One potential disadvantage, however, is that the ferrite box 702 can increase the overall weight of the charger, but this can be a suitable trade off. Also, the area of PCB 704 is somewhat reduced as a cutout area 706 needs to be made in the center of the PCB 704 to accommodate the battery 514 and ferrite box structure 702. Coil 108 can comprise a coil that is wrapped in a racetrack, planar configuration around the outer edge of the PCB 704, with the associated electronic circuitry 508 printed onto the side of the PCB 704 opposite the coil 108. Again, the use of a thin prismatic battery rather than a cylindrical battery in the charger allows for a low-profile external charger housing.

Figure 8:
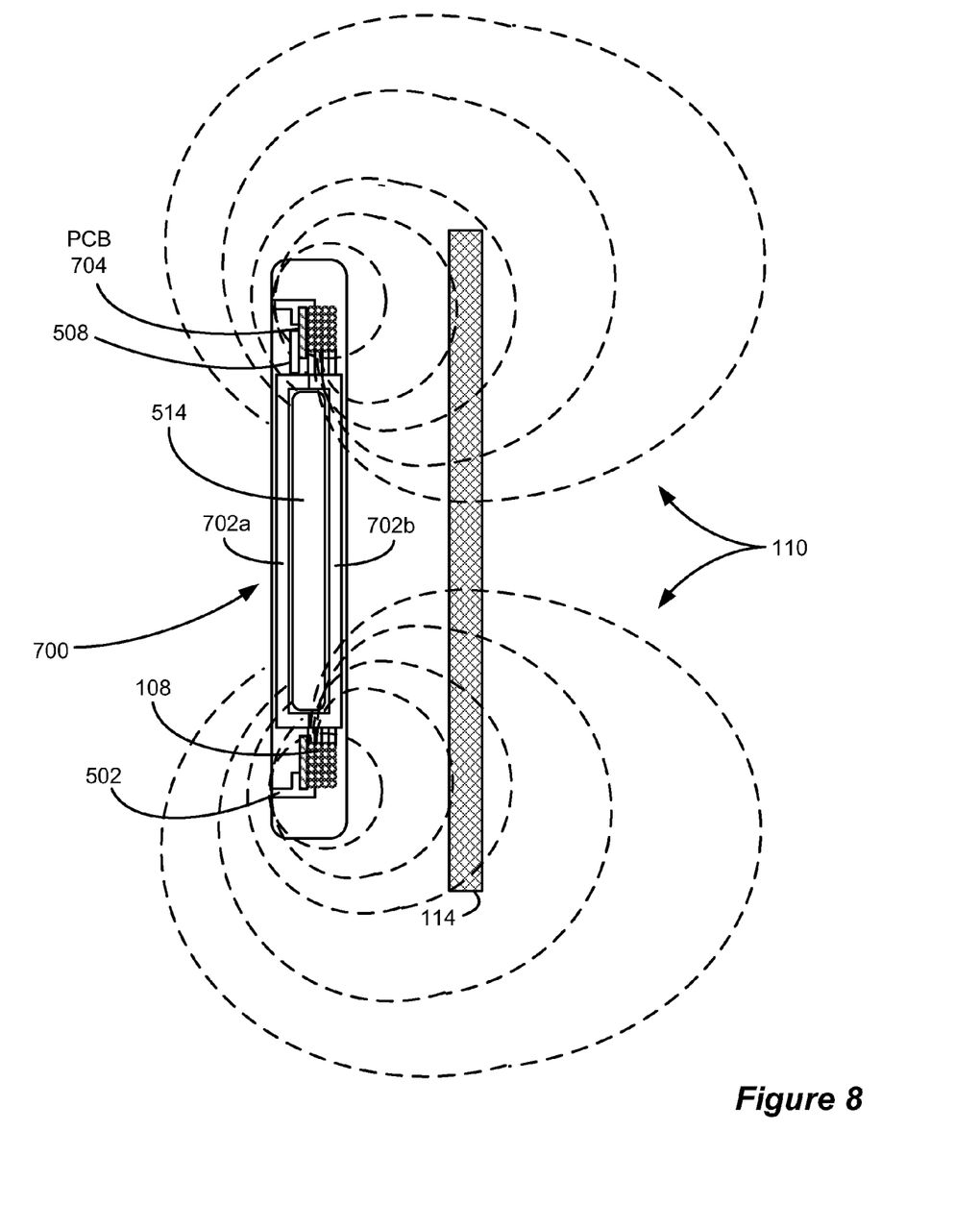
FIG. 8 shows a side view of representative magnetic field lines generated by the external charger of FIGS. 7A and 7B.

FIG. 8 shows a side view of representative magnetic field lines 110 generated by the external charger 700 of FIGS. 7A and 7B. Similar to FIG. 6, it can be seen that the ferrite box 702 increases the overall efficiency of the charging system due to fewer magnetic field lines being directed backwards and away from the patient's body, where the magnetic field energy is wasted. A higher percentage of the magnetic field 110 from the primary coil 108 is directed towards the implanted secondary coil across skin boundary 114, though the effect is not as great as that seen in FIG. 6 due to the particular arrangement required to accommodate the ferrite box 702 within the extent of the coil. However, the ferrite box 702 does provide for superior shielding of the battery 514 from eddy currents created by field lines 110 in the battery 514's casing.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external device for use with an implantable medical device, comprising:
    a housing;
    a coil within the housing;
    a battery within the housing;
    a printed circuit board (PCB) within the housing of the external device; and
    a magnetic shield within the housing comprising a high permeability material,
    wherein the magnetic shield is adhesively attached to the PCB,
    wherein the coil, the magnetic shield, and the battery are aligned in a stack,
    wherein the magnetic shield is located between the battery and the coil in the stack,
    wherein the magnetic shield and coil are located on a first side of the PCB, and the battery is located on a second side of the PCB, and
    wherein the coil generates a magnetic field to provide power to the implantable medical device.

2. The device of claim 1, wherein the magnetic shield comprises at least one ferrite plate.

3. The device of claim 1, wherein the battery comprises a rechargeable Lithium-ion battery.

4. The device of claim 1, wherein the magnetic shield covers the entire extent of the coil.

5. The device of claim 1, wherein the coil, battery, and magnetic shield are co-axially aligned in the stack.

6. The device of claim 1, wherein the magnetic shield comprises a plurality of plates.

7. An external device for use with an implantable medical device, comprising:
    a housing;
    a coil within the housing;
    a battery within the housing;
    a printed circuit board (PCB) within the housing of the external device; and
    a magnetic shield within the housing comprising a high permeability material,
    wherein the coil, the magnetic shield, and the battery are aligned in a stack, wherein the magnetic shield is located between the battery and the coil in the stack,
    wherein the magnetic shield and coil are located on a first side of the PCB, and the battery is located on a second side of the PCB, and
    wherein the coil generates a magnetic field to provide power to the implantable medical device.

8. The device of claim 7, wherein the magnetic shield comprises at least one ferrite plate.

9. The device of claim 7, wherein the battery comprises a rechargeable Lithium-ion battery.

10. The device of claim 7, wherein the magnetic shield covers the entire extent of the coil.

11. The device of claim 7, wherein the coil, battery, and magnetic shield are co-axially aligned in the stack.

12. The device of claim 7, wherein the magnetic shield comprises a plurality of plates.

13. An external device for use with an implantable medical device, comprising:
    a housing;
    a coil within the housing;
    a battery within the housing;
    a printed circuit board (PCB) within the housing of the external device; and
    a magnetic shield within the housing comprising a high permeability material,
    wherein the coil, the magnetic shield, and the battery are aligned in a stack, wherein the magnetic shield is located between the battery and the coil in the stack,
    wherein the magnetic shield and battery are located on a first side of the PCB, and the coil is located on a second side of the PCB, and
    wherein the coil generates a magnetic field to provide power to the implantable medical device.

14. The device of claim 13, wherein the magnetic shield comprises at least one ferrite plate.

15. The device of claim 13, wherein the battery comprises a rechargeable Lithium-ion battery.

16. The device of claim 13, wherein the magnetic shield covers the entire extent of the coil.

17. The device of claim 13, wherein the coil, battery, and magnetic shield are co-axially aligned in the stack.

18. The device of claim 13, wherein the magnetic shield comprises a plurality of plates.

19. An external device for use with an implantable medical device, comprising:
    a housing;
    a coil within the housing;
    a battery within the housing;
    a printed circuit board (PCB) within the housing of the external device; and
    a magnetic shield within the housing comprising a high permeability material,
    wherein the magnetic shield is adhesively attached to the PCB,
    wherein the coil, the magnetic shield, and the battery are aligned in a stack,
    wherein the magnetic shield is located between the battery and the coil in the stack,
    wherein the magnetic shield and battery are located on a first side of the PCB, and the coil is located on a second side of the PCB, and
    wherein the coil generates a magnetic field to provide power to the implantable medical device.

20. The device of claim 19, wherein the magnetic shield comprises at least one ferrite plate.

21. The device of claim 19, wherein the magnetic shield covers the entire extent of the coil.

22. The device of claim 19, wherein the coil, battery, and magnetic shield are co-axially aligned in the stack.

23. The device of claim 19, wherein the magnetic shield comprises a plurality of plates.

* * * * *